(12) United States Patent
Davis et al.

(10) Patent No.: US 10,648,962 B2
(45) Date of Patent: May 12, 2020

(54) SYSTEM AND METHOD FOR PREVENTING CELL PHONE USE WHILE DRIVING

(71) Applicant: Text Free Enterprises, LLC, Deer Park, NY (US)

(72) Inventors: Todd M. Davis, Coram, NY (US); Thomas DeGasperi, Middle Island, NY (US); Gary Hancock, Centereach, NY (US)

(73) Assignee: TEXT FREE ENTERPRISES, LLC, Deer Park, NY (US)

( * ) Notice: Subject to any disclaimer, the term of this patent is extended or adjusted under 35 U.S.C. 154(b) by 0 days.

(21) Appl. No.: 16/244,178

(22) Filed: Jan. 10, 2019

(65) Prior Publication Data
US 2019/0145946 A1   May 16, 2019

Related U.S. Application Data

(63) Continuation-in-part of application No. 15/685,000, filed on Aug. 24, 2017, now Pat. No. 10,182,137.

(60) Provisional application No. 62/383,216, filed on Sep. 2, 2016.

(51) Int. Cl.
*G06F 3/041* (2006.01)
*G01N 33/00* (2006.01)
*B60W 40/08* (2012.01)

(52) U.S. Cl.
CPC ..... *G01N 33/0063* (2013.01); *G01N 33/0036* (2013.01); *B60W 40/08* (2013.01); *B60W 2040/0818* (2013.01); *B60W 2540/24* (2013.01); *G01N 33/0047* (2013.01)

(58) Field of Classification Search
CPC .......... G01N 33/4972; G01N 33/0063; G01N 33/0036; G01N 33/0047; B60W 40/08; B60W 2040/0818; B60W 2540/24; G01P 3/00
See application file for complete search history.

(56) References Cited

U.S. PATENT DOCUMENTS

| | | | |
|---|---|---|---|
| 6,351,989 B1 * | 3/2002 | Foss | B60H 1/008 73/117.01 |
| 8,527,013 B2 * | 9/2013 | Guba | H04W 4/027 455/569.2 |
| 9,167,418 B1 | 10/2015 | Tuluca | |

(Continued)

OTHER PUBLICATIONS

Drive Alert Now "Drive Alert for Your Family, How to Prevent Teens Texting While Driving" Publication (online), Aug. 3, 2016, Retrieved from the internet.

*Primary Examiner* — An T Nguyen
(74) *Attorney, Agent, or Firm* — Arent Fox LLP

(57) ABSTRACT

A system and method is provided for monitoring a vehicle for inhibiting substances comprising detecting, using a movement detector, movement of a vehicle, collecting, using an air sampler, an initial air sample of air within a cabin of the vehicle, analyzing, using an inhibiting substance detector, the air sample to determine whether an inhibiting substance is detected in the air sample, in response to determining that an inhibiting substance is detected in the air sample, increasing the sampling rate of the air sampler, until a predetermined number of samples are collected that also have been analyzed and an inhibiting substance detected therein and sending an alert to an administrator of the vehicle indicating that inhibited driving is occurring.

19 Claims, 10 Drawing Sheets

(56) References Cited

U.S. PATENT DOCUMENTS

| | | |
|---|---|---|
| 2009/0309787 A1 | 12/2009 | Gildea |
| 2010/0043524 A1* | 2/2010 | Takata ................. B60K 28/063 |
| | | 73/23.3 |
| 2011/0021234 A1 | 1/2011 | Tibbitts et al. |
| 2016/0073324 A1 | 3/2016 | Guba et al. |
| 2016/0349239 A1* | 12/2016 | Chien ................. G01N 33/4972 |
| 2017/0057353 A1* | 3/2017 | Griffin ................. B60K 28/063 |
| 2017/0096145 A1* | 4/2017 | Bahn ........................ B60Q 9/00 |
| 2017/0106715 A1* | 4/2017 | Duan ................. B60H 1/00764 |
| 2017/0132521 A1* | 5/2017 | Xu ......................... G06N 5/046 |
| 2018/0095586 A1* | 4/2018 | Cho ....................... G06F 1/3262 |
| 2018/0235581 A1* | 8/2018 | Vianello ................... G01V 8/10 |
| 2019/0092342 A1* | 3/2019 | Biondo ................ A61B 5/4845 |
| 2019/0113502 A1* | 4/2019 | Ruland .............. G01N 33/4972 |
| 2019/0145946 A1* | 5/2019 | Davis ................. G01N 33/0063 |

* cited by examiner

Fig. 4A

SYSTEM AND METHOD FOR PREVENTING CELL PHONE USE WHILE DRIVING

CROSS REFERENCE TO RELATED APPLICATIONS

This application is a continuation in part of U.S. patent application Ser. No. 15/685,000 filed on Aug. 24, 2017 which claims priority to U.S. Patent Provisional No. 62/383, 216, filed Sep. 2, 2016, the entire contents of each of which are hereby incorporated by reference.

FIELD OF TECHNOLOGY

The present disclosure generally relates to controlling cell phone operation, and, more, specifically, to a system and method for preventing cell phone use while driving.

BACKGROUND

In recent years, the U.S. Department of Transportation has launched numerous programs and initiatives to reduce traffic-related fatalities and injuries. Moreover, many states explicitly prohibit talking, text-messaging or playing video games on hand-held mobile phones while driving. Additionally, a number of states, such as California, have passed laws banning or restricting young drivers (under age 18) from using mobile phones, or other types of mobile devices while driving. However, despite these attempts by the federal government and various states from protecting drivers from causing traffic related incidents as a result of cell phone use while driving, it is apparent that many drivers (especially teenage drivers) tend to ignore these rules.

For example, nearly half of all high school students sixteen and older text and email while driving. Moreover, nearly one fourth of teenage drivers say they answer at least one text message every time they drive. In fact, current statistics reveal that eleven teen drivers die every day while texting and driving. Teenage drivers are four times more likely to get into a distracted driving accident than their parents and teen texting and driving makes them twenty-three times more likely to crash.

Accordingly, a system is needed to prevent distracted driving by eliminating cell phone use during driving. While certain technologies exist that help reduce these problems, there are also current technological restrictions for certain cell phones, such as Apple's iPhone® that inhibit a software application's ability to effectively block the operation of the iPhone during a specified time (e.g., while the user of the mobile device is driving).

SUMMARY

According, as described herein, the proposed method and system provides an effective blocking solution to lock a cell phone. In general, on all Apple iPhones® (and other mobile devices, the user can press the power button and that will power down the screen (lock the phone). However, there is no way to programmatically press the power button via application installed. However, if the cell phone is connected to a wireless Bluetooth keyboard, the user can press the power button on the keyboard and that power command will be sent to the phone. Moreover, the cell phone will be locked and phone calls (and other user actions) will be disconnected just as if user pressed the power button. Thus, according to the disclosure herein, the system and method circumvents any control by the operating system of the cell phone to restrict such controls by software applications.

Thus, a system and method is provided for preventing cell phone use while driving. The method includes determining by a cell phone if the speed of the vehicle is greater than zero miles per hour, and, if so, transmitting a command request to a locking module wirelessly coupled to the mobile device. In response to the command request, the microcontroller generates a locking operation signal that is sent to the cell phone. Upon receipt, the cell phone locks operation of the device by a user.

Moreover, according to an exemplary aspect, the system includes a microcontroller; and a mobile device wirelessly coupled to the microcontroller. In this regard, the mobile device includes a transceiver configured to receive data indicating a speed of the vehicle, and a processor configured to determine whether the speed of the vehicle is greater than zero miles per hour, and, if the speed is greater than zero miles per hour, generate a command request to be transmitted to the microcontroller. According to the disclosed system in response to the command request, the microcontroller is configured to generate and transmit a locking operation signal to the mobile device. Moreover, the mobile device locks operation upon receipt of the locking operation signal.

Furthermore, according to an exemplary aspect, a system and method is provided for inhibiting substances, comprising detecting, using a movement detector, movement of a vehicle, collecting, using an air sampler, an initial air sample of air within a cabin of the vehicle, analyzing, using an inhibiting substance detector, the air sample to determine whether an inhibiting substance is detected in the air sample, in response to determining that an inhibiting substance is detected in the air sample, increasing the sampling rate of the air sampler, until a predetermined number of samples are collected that also have been analyzed and an inhibiting substance detected therein and sending an alert to an administrator of the vehicle indicating that inhibited driving is occurring.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplary pointed out in the claims.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

FIGS. 4A and 4B illustrate screenshots of the software application providing alerts and settings information to a user according to an exemplary aspect.

DETAILED DESCRIPTION

Figure 1:
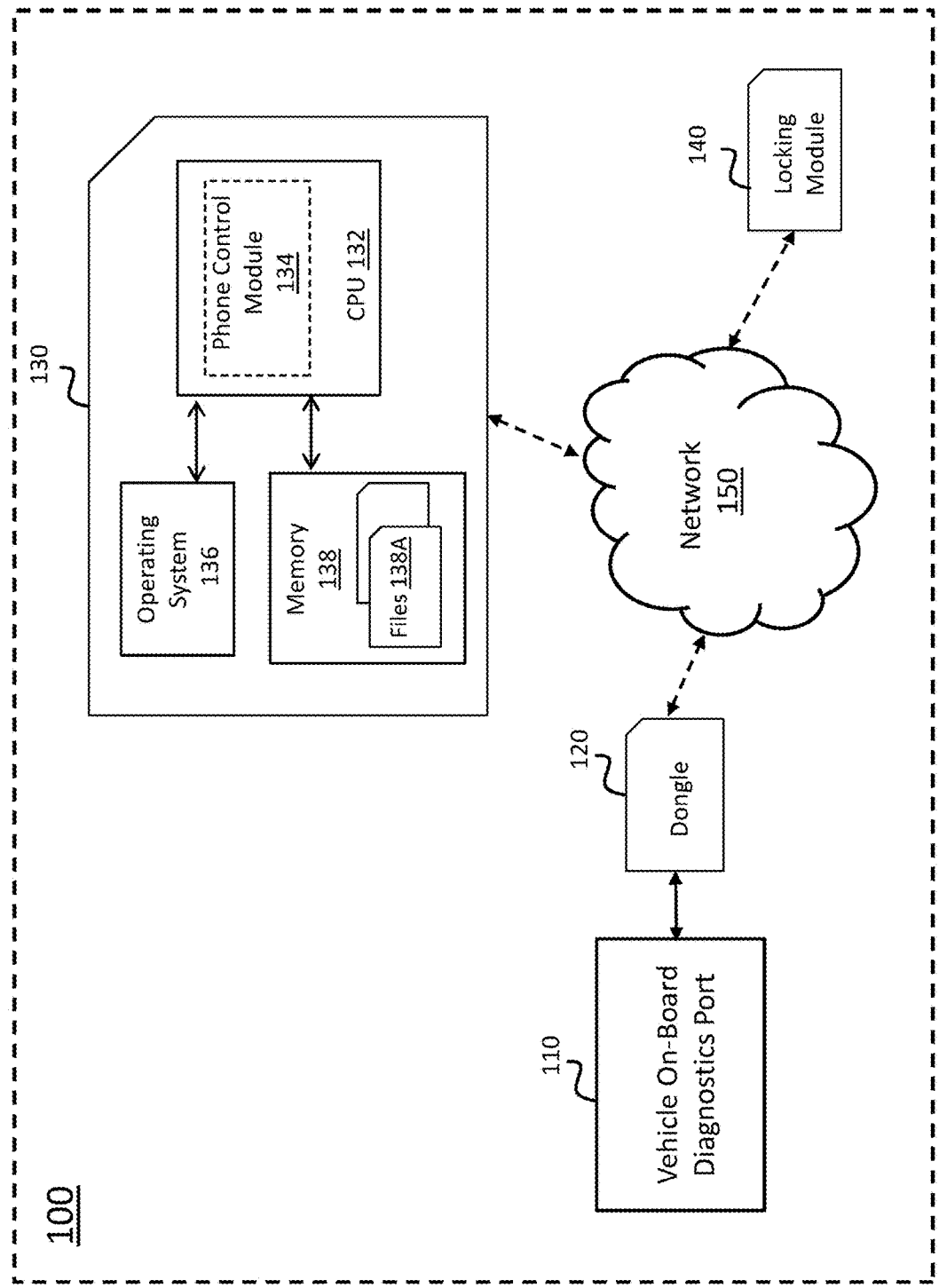
FIG. 1 is a block diagram illustrating the system for preventing cell phone use while driving according to an exemplary aspect.

Various aspects of the invention are now described with reference to the drawings, wherein like reference numerals are used to refer to like elements throughout. In the following description, for purposes of explanation, numerous specific details are set forth in order to promote a thorough understanding of one or more aspects of the invention. It may be evident in some or all instances, however, that any aspects described below can be practiced without adopting the specific design details described below. In other instances, well-known structures and devices are shown in block diagram form in order to facilitate description of one or more aspects. The following presents a simplified summary of one or more aspects of the invention in order to provide a basic understanding thereof.

FIG. 1 is a block diagram illustrating the system for preventing cell phone use while driving according to an exemplary aspect. In general, it is contemplated that the system 100 is provided within a vehicle to control/prevent operation of a mobile device 130 while the vehicle is in operation and/or moving. As shown, the system 100 includes a vehicle on-board diagnostics ("OBD") port 110, a dongle 120, the mobile device 130, a locking module 140, and a network 150 that facilitates wireless communication between the devices, include the dongle 120, the mobile device 130 and the locking module 140. In this aspect, the network 150 can be, for example, a personal area wireless network using Bluetooth communication technology and protocols in which each of the devices is configured to communicate with one another using short-wavelength UHF radio waves, for example. The wireless communication is illustrated by dashed two-way arrows from devices 120, 130, and 140 to and from network 150. In the exemplary aspect, the mobile device 130 communicates directly with each of the dongle 120 and the locking module 140 using Bluetooth communication. More particularly, the dongle 120 first communicates with the mobile device 130 using Bluetooth and then the mobile device 130 communicates with the locking module using Bluetooth communication. In an alternative embodiment, the dongle 120 and the locking module 140 can communicate directly with each other using Bluetooth communication.

Moreover, according to the exemplary aspect, the dongle 120 is provided to obtain the vehicles speed and other information (e.g., engine operation, etc.) from the vehicle's OBD system.

As is known to those skilled in the art, the vehicle's OBD system provides self-diagnostic and reporting capability that can enable a vehicle owner or mechanic to access information about the engine and other vehicle sub-systems. Moreover, currently manufactured motor vehicles are now equipped with a standard OBD-II or EOBD connector port. The OBD connection port can provide real-time engine data (including vehicle speed) in addition to standardized diagnostic trouble codes that allow a mechanic to rapidly identify and remedy problems with the vehicle.

In the exemplary aspect, the dongle 120 can be, for example, an OBD-2 dongle that includes a physical connector that can be plugged into (i.e., mated with) the OBD port 110, preferably on a long-term basis, to receive the OBD data, such as vehicle speed, and power. The connection between dongle 120 and OBD port 110 is illustrated by a solid two-way arrow. In addition to the preferred implementation (i.e., to block cell phone operation during vehicle operation), it is contemplated that the dongle 120 can also automatically track driving habits (e.g., speeding incidents, and the like) and provide reporting information that can be sent to a parent's computing device, for example.

The hardware of existing dongles is well known in the art and will not be described in detail herein. However, according to the exemplary aspect, the dongle 120 can include a processor (e.g., a microcontroller), optional memory (such as a flash memory), a short-range wireless transceiver, as well as other various hardware components. The wireless transceiver is provided for pairing with the mobile device 130 to wirelessly transmit OBD data. Thus, during operation, the dongle 120 is configured to receive the OBD data from the OBD port 110 while the vehicle is in operation/moving (e.g., "on" and "off" states of the engine as well as non-zero values for speed, for example) and transmit this data in real-time to the mobile device 130 using the transceiver for Bluetooth communication via network 150. In an alternative aspect, the dongle 120 may temporarily store the OBD data in memory and transmit the OBD to the mobile device 130 on a periodic basis (e.g., once per second or the like) or in response to a prompting request from the mobile device 130.

Figure 5:
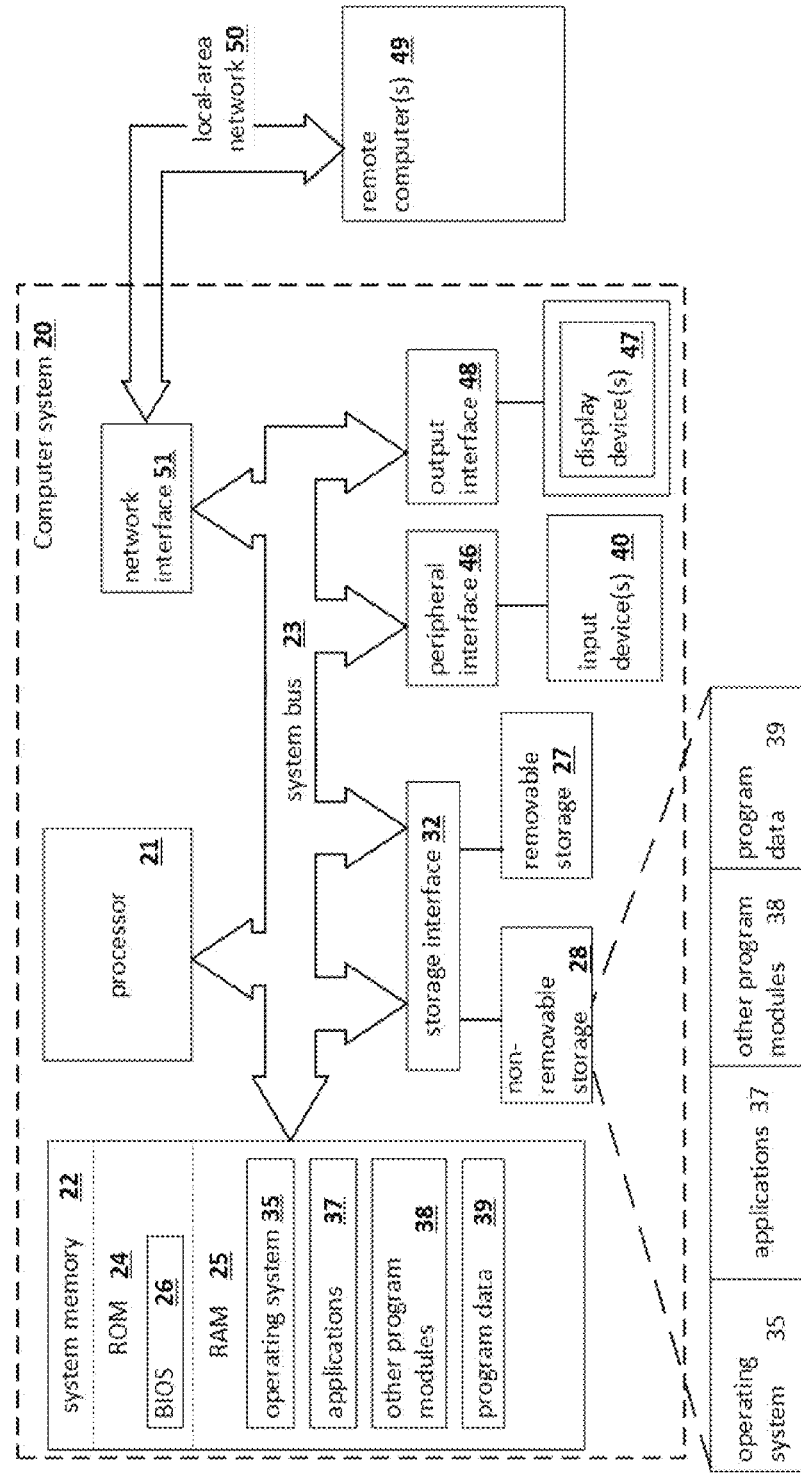
FIG. 5 illustrates an example of a general-purpose mobile device on which the disclosed systems and method can be implemented.

Furthermore, the mobile device 130 can be a smartphone, such as Apple iPhone®, that includes a computer-processing unit ("CPU") 132, an operating system 136 (e.g., Apple iOS) and memory 138. An example of the hardware of the mobile device 130 is shown in FIG. 5 and will be described in detail below. However, in general, a phone control module 134 (e.g., a downloadable software application from an "Apps store") is provided that includes software code (e.g., processor executable instructions) in memory, which may be configured to execute/facilitate the algorithms described herein. CPU 132 is configured to execute the phone control module 134, as will be described in greater detail below. Furthermore, memory 138 is provided to store OBD data received from dongle 120 and can be a typical computer-readable medium including data storage that can be found on a smartphone, such as RAM, ROM, EEPROM, flash memory or the like.

Moreover, as used herein, the term "module" refers to a software service or application executed on the various devices and is implemented using a combination of the specific device's hardware and software, such as by the microcontroller and a set of instructions to implement the module's functionality, which (while being executed) transform the microcontroller system into a special-purpose device. Each module can also be implemented as a combination of the two, with certain functions facilitated by hardware alone, and other functions facilitated by a combination of hardware and software. Each module can be realized in a variety of suitable configurations, and should not be limited to any example implementation exemplified herein.

As further shown in FIG. 1, system 100 includes the locking module 140, which is a programmable Bluetooth communication module according to the exemplary aspect. For example, an off-the-shelf programmable module, such as the HC-08 Bluetooth UART Communication Module, can be implemented as the microcontroller of the locking module 140. The details of locking module 140 will be described below with respect to FIG. 2, but locking module 140 generally is a module that has been programmed to act and emulate as a wireless keyboard in communication with mobile device 130. In this manner, the locking module 140 is configured to emits a wireless Bluetooth signal that makes mobile device 130 (e.g., an Apple iPhone®) think that that the locking module 140 is a wireless keyboard. As a result, after this signal (module) is paired with the mobile device 130, the locking module 140 can send the lock command, which will not be blocked by the operating system 136 of the mobile device 130.

Furthermore, the locking module 140 is programmed to accept commands (and related data) using the Bluetooth communication protocols from the mobile device 130 as well. Thus, according to the exemplary aspect, when speed is detected by dongle 120 and transmitted to mobile device 130, the mobile device 130 (that is unlocked) can send the data to locking module 140, which, in turn, sends the lock command back to the mobile device 130. In one aspect, because the mobile device 130 tells the locking module 140 when the lock command should be sent, the mobile device 130 can also ensure that the phone is not locked if an emergency phone operation (e.g., dial "9-1-1") needs to be initiated, for example.

Figure 2:
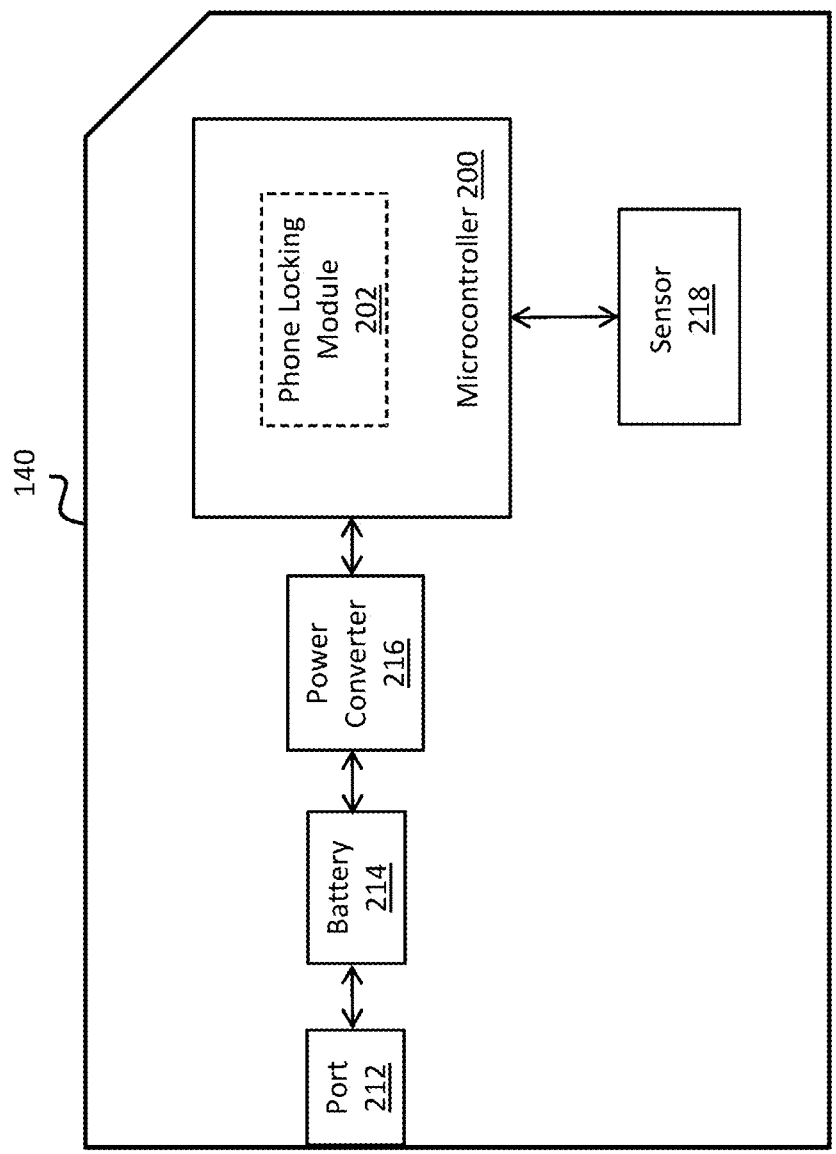
FIG. 2 is a block diagram illustrating the locking module 140 for preventing cell phone use while driving according to an exemplary aspect.

FIG. 2 is a block diagram illustrating the locking module 140 for preventing cell phone use while driving according to an exemplary aspect. As noted above, the locking module 140 can include a microcontroller 200, which can be, for example, the HC-08 Bluetooth UART Communication Module according to one exemplary aspect. The hardware components of such a module are well known and will not be repeated herein. The datasheet for the HC-08 module is described at: http://www.wavesen.com/mysys/db_picture/news3/2015121885146101.pdf, the contents of which are hereby incorporated by reference. As described therein, the HC-08 module firmware operates at a working voltage between 2 volts to 3.6 volts and operates in a range of 8 to 10 meters. Moreover, the HC-08 module is an ultra-low power Bluetooth protocol v4.0 module that can operate as either a master or a slave device. The microcontroller 200 of the locking module 140 can include pins, e.g., VCC (Pin 12) and GND (Pin 13), provided for power consumption. It should be appreciated that the microcontroller 200 of the locking module 140 is not limited to the HC08 module. Rather, the HC-08 module is a cheaper alternative to HC-10 (which can also be used). Moreover, the Texas Instrument® chip (CC2540) can also be utilized (http://www.ti.com/product/CC2540), for example.

As described above, the microcontroller 200 of the locking module 140 is pre-programmed to receive vehicle speed information (and other ODB data, for example) from the mobile device 130 and generate locking signals in response. In this regard, microcontroller 200 can be pre-programmed with the phone locking module 202, which is configured to perform these functions. Moreover, referring to the HC-08 module, for example, the PIO01 (Pin 32) or PIO00 (Pin 34) should be connected to the VCC (Pin 12), according to the exemplary aspect. In operation, these pins will instruct the locking module 140 when it should start to advertise itself (using Bluetooth communication) so that the mobile device 130 (e.g., an Apple iPhone®) can detect and interpret the locking mobile 140 as a keyboard device. In this aspect, the mobile device 130 will only be able to connect to the locking module 140 while the locking module 140 is transmitting such a signal. Once the locking module 140 is connected, it will maintain the connection and such an advertising signal is not required. Of course, during re-connect, the locking module 140 will need to transmit the advertising signal again.

Additional components of the locking module 140, as shown in FIG. 2, include a rechargeable battery 214, a port 212 (such as a USB port) that facilitates the charging of the rechargeable battery 214 (by a USB cable, for example), and a power converter 216 that converts power from the rechargeable battery 214 to the microcontroller 200 during operation. Optionally, the locking module 140 can also include one or more sensors 218, such as a sound sensor that is configured to initiate the advertising signal to the mobile device 130 once sound is detected. In other words, the locking module 140 may be kept in the automobile of the user. It will then only begin the connection process to the mobile device 130 if sensor 218 detects sound in the vehicle. Furthermore, although not specifically shown, the locking module can include a plastic board (to second the various components) and an outer casing for further protection.

Figure 3A:
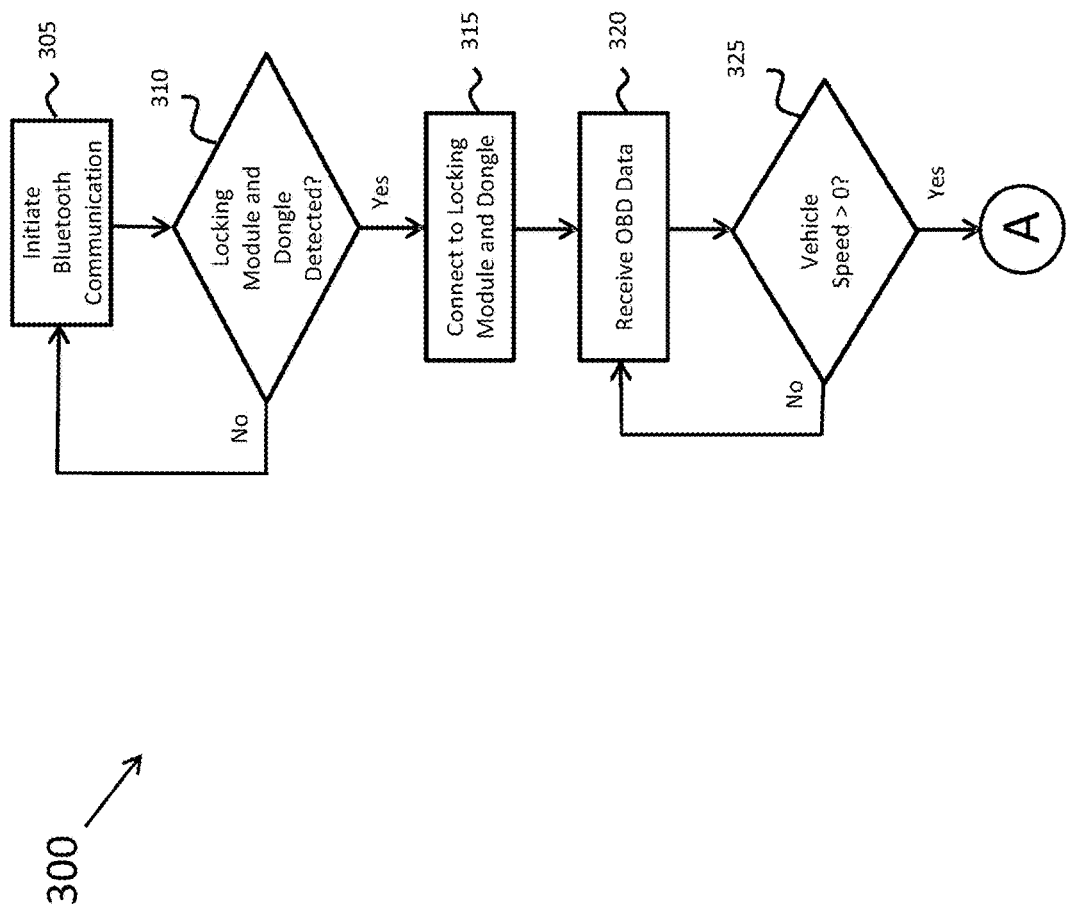
FIGS. 3A and 3B illustrate a flowchart of a method for preventing cell phone use while driving according to an exemplary aspect.
Figure 3B:
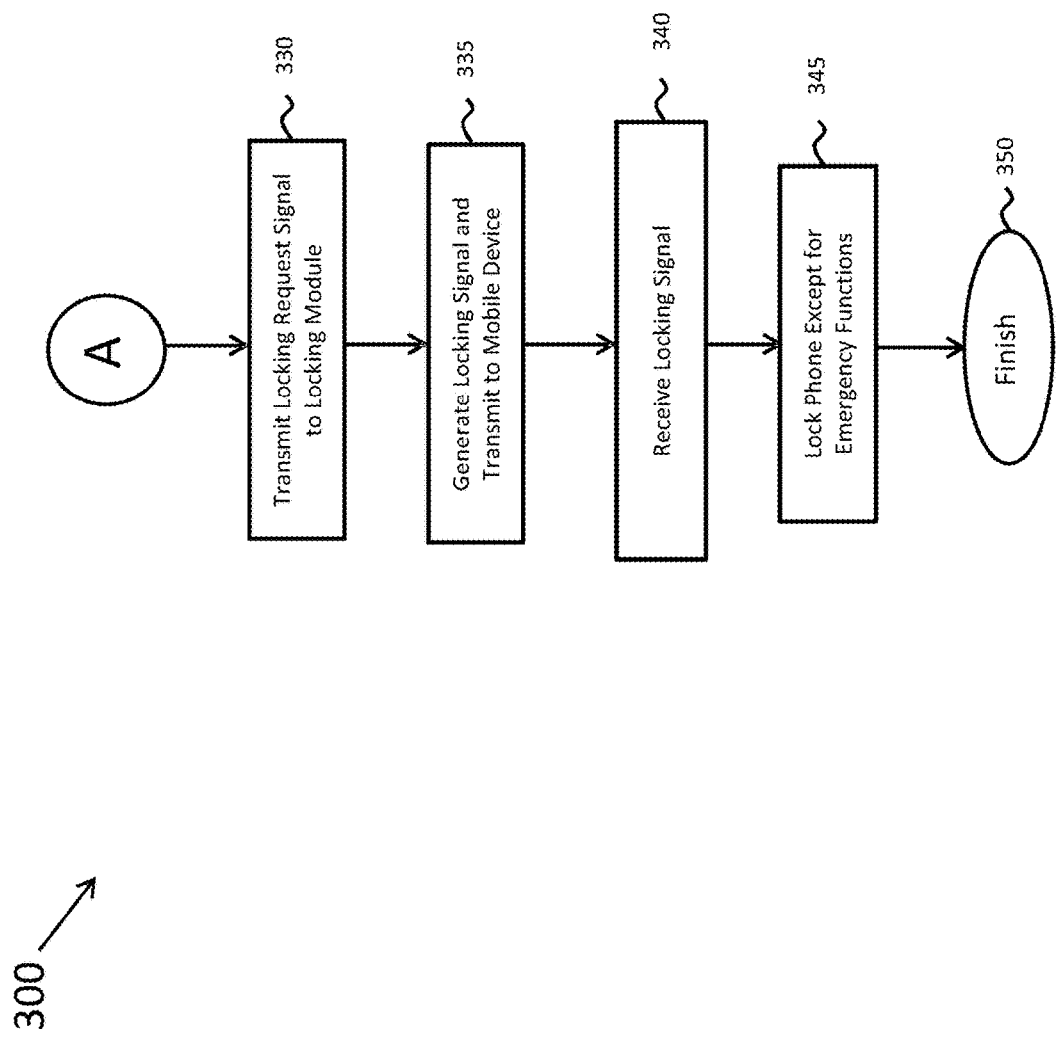

FIGS. 3A and 3B illustrate a flowchart of a method for preventing cell phone use while driving according to an exemplary aspect. Initially, at step 305, the mobile device 130 initiates wireless (e.g., Bluetooth) communication between each of the dongle 120 and the locking module 140. In particular, the mobile device 130 can sending a scanning/pairing signal to detect any devices (within range) that are configured to communicate by Bluetooth. Alternatively, or in addition as described above, the locking module 140 can transmit an advertising signal requesting pairing with the mobile device 130. In either case, at step 310, the mobile device 130 determines whether the dongle 120 and locking module 140 are detected. If so, at step 315, the mobile device 130 and each of the dongle 120 and locking module 140 are paired for wireless communication. If not, the method returns to step 305 to initiate Bluetooth communication. It should be appreciated that while steps 310 and 315 are illustrated as the mobile device 130 pairing with each of the dongle 120 and locking module 140 concurrently, these connection processes can also be performed in sequence.

In either case, once the dongle 120 and mobile device 130 are paired, the dongle 120 begins receiving OBD data (including vehicle speed) from the OBD port 110 and dynamically (i.e., in real-time) transmitting the vehicle speed to the mobile device 130, at step 320. In an alternative aspect, it is contemplated that the dongle 120 can be paired directly with the locking module 140 and can transmit the vehicle speed directly to the locking module 140.

At step 325, the mobile device 130, and, in particular phone control module 134, determines whether the vehicle speed is greater than 0 miles per hour ("MPH"). In other words, the phone control module 134 uses the received OBD data to determine whether the vehicle is moving. In an alternative aspect, the OBD data could indicate an engine "ON" status or the like to confirm that the vehicle is in operation. Other indications including detecting noise/sounds as discussed above, sensing vibration, sensing voltage in the ODB port 110, and the like. Any such data can be used as the trigger to block phone operation, although it is contemplated that the vehicle speed is the indicator in the exemplary aspect.

As further shown in FIG. 3A, if the OBD data indicates that the vehicle speed is not greater than 0 MPH, then the method returns to step 320 where the mobile device continues to receive OBD data from dongle 120. However, if the vehicle speed is greater than 0 MPH, the method proceeds to step 330 shown in FIG. 3B.

Specifically, a step 330, if the phone control module 134 determines that the vehicle is moving and that the phone is unlocked, the mobile device 130 transmits a control command to the locking module 140 request that a lock command be sent back to the mobile device 130. At step 335, the locking module 140 generates a locking command and sends it back to the mobile device 130. In general, a mobile device, such as an Apple iPhone® can be locked if a user presses the power button to power down the screen and effectively lock the phone. However, the operating system (e.g., iOS) of the phone prevent(s) an application installed on the phone from mimicking the power down button command. Thus, according to the exemplary aspect, the mobile device 130 interprets the signals receiving from the locking module 140 as signals from a wireless keyboard. Moreover, wireless keyboards can effectively transmit locking signals to an Apple iPhone® and the operating system will accept these signals and lock the phone. In this manner, the phone will be locked, user operations (e.g., text and activating applications) will be blocked, and any phone calls will be disconnected. Thus, according to the exemplary aspect, the locking command sent from the locking module 140 to the mobile device 130 as interpreted as a locking command received from a wireless keyboard, which effectively locks the phone. Accordingly, as shown, the mobile device receives the signal at step 340 and is locked at step 345. In this aspect, the phone will typically phone be locked, unless the user request that he or she wants to place an emergency phone call, as described herein. The method finishes at step 350.

In one aspect, the locking module 140 (i.e., the locking command) mimics the wireless keyboard signal by using the HID ("human interface device") Profile that the iPhone recognizes as a native wireless keyboard. In general, the HID profile uses the universal serial bus ("USB") definition of the mobile device in order to leverage the existing class drivers for such devices. The HID profile describes how to use the USB HID protocol to discover a HID class device's feature set and how a Bluetooth enabled device can support HID services. The HID profile is designed to enable initialization and control self-describing devices as well as provide a low latency link with low power requirements. In the exemplary aspect, the locking module 140 must be paired with the mobile device 130 (e.g., the iPhone) upon first time use and after that iPhone will maintain the paired connection, as described herein. A power command is sent to the iPhone that locks the phone over Bluetooth signal according to an exemplary aspect, and this power signal will disconnect the phone call if it's in progress or lock the screen if phone is being used.

Figure 4A:
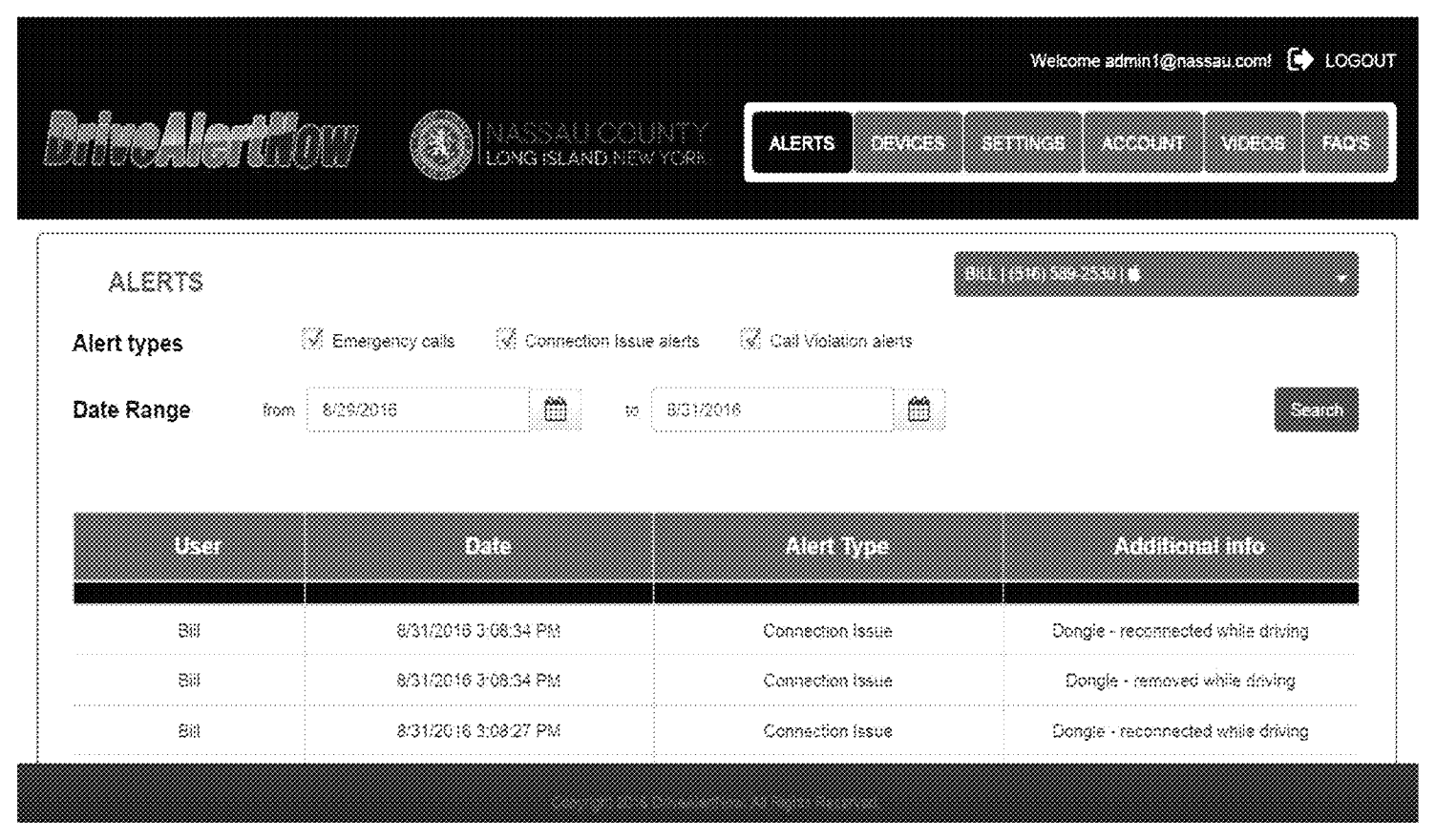
Figure 4B:
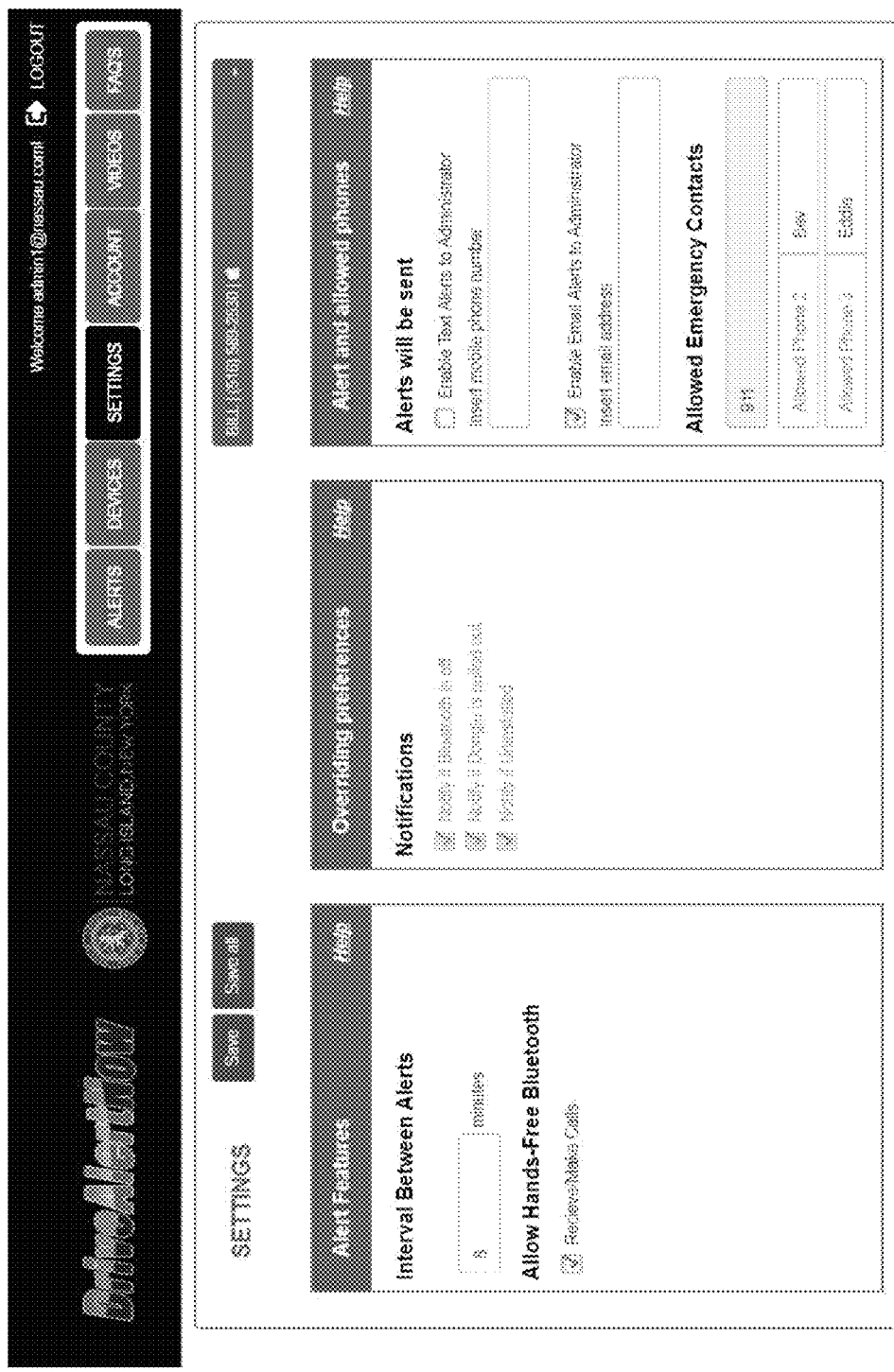

It should be appreciated that the locking operation on the mobile device 130 is maintained as long as the vehicle is in moving or in operation. Moreover, the phone control module 134 include capabilities that enable it to communicate with a server to log violations and misconfiguration of its settings. In particular, when the phone control module 134 is downloaded on the mobile device 130, which can be a teenage driver's phone for example, the parent can access a website that controls the configurations of the application (e.g., identifying the teenager's phone as being controlled by the application). In addition, the mobile device 130 transmits the driving data, alerts (see screenshot in FIG. 4A), dashboard settings and possible misconfigurations (see screenshot in FIG. 4B), etc., to a server that enables the parent to view the teenager's compliance with the system when the parent logs onto the website connected with the application and server.

Thus, according to the exemplary aspect, OBD data is provided by the dongle 120 to the mobile device 130, where it is interpreted to determine whether a request to the locking module 140 for a locking command should be generated. According to an alternative aspect, the vehicle speed data can be generated directly from the mobile devices 130's GPS system. However, this aspect has limitations in that GPS and speed data will be generated even if the user is walking. Thus, restrictions would likely be required to implement this aspect, such as defining a minimum speed for when the locking command is requested (e.g., the speed must be over 10 MPH). In yet another aspect, the OBD data can be transmitted directly from the dongle 120 to the locking module 140. However, this aspect has limitation in terms of the phone's ability to make emergency calls and the like. In other words, if the user has dialed "9-1-1", the system would not want to receive a locking signal from the locking module 140 that would disconnect the call. In contrast, according to the exemplary aspect, the phone control module 134 determines when a request is sent to the locking module 140 to request a locking command. In this regard, the phone control module 134 will not send this request if the phone is currently being used for an emergency service, for example.

In a further aspect, a compass can be used in place of the dongle to detect movement of the vehicle. The compass could be a stand-alone device in communication with the mobile device 130 and/or locking module 140, or can be a component (software or hardware) of either the mobile device 130 and/or locking module 140. In one aspect, any variation in the direction of the compass will inherently mean that the vehicle is moving (assuming the compass is fixed relative to the vehicle). Thus, upon a detection of movement, the locking algorithm described above can be implemented. Other sources of speed and/or movement of the vehicle can include a GPS module added into the locking module 140, a detection of a power fluctuation in the car's power outlet (by the dongle 120 or mobile phone 130 or locking module 140, for example), a detection of movement by monitoring outside car conditions (e.g., using a camera to detect change), sensors detecting vibration or sound (as discussed above) from the car, and the like. Such detections method can be implemented using the techniques described herein as should be appreciated.

FIG. 5 is a block diagram illustrating a computer system 20 on which aspects of systems and methods for multi-threaded access to cloud storage may be implemented in accordance with an exemplary aspect. It should be noted that the computer system 20 can correspond to computer 200 for example, described earlier. The computer system 20 can be in the form of multiple computing devices, or in the form of a single computing device, for example, a desktop computer, a notebook computer, a laptop computer, a mobile computing device, a smart phone, a tablet computer, a server, a mainframe, an embedded device, and other forms of computing devices.

As shown, the computer system 20 includes a central processing unit (CPU) 21, a system memory 22, and a system bus 23 connecting the various system components, including the memory associated with the central processing unit 21. The system bus 23 may comprise a bus memory or bus memory controller, a peripheral bus, and a local bus that is able to interact with any other bus architecture. Examples of the buses may include PCI, ISA, PCI-Express, Hyper-Transport™, InfiniBand™, Serial ATA, I²C, and other suitable interconnects. The central processing unit 21 (also referred to as a processor) can include a single or multiple sets of processors having single or multiple cores. The processor 21 may execute one or more computer-executable code implementing the techniques of the present disclosure. The system memory 22 may be any memory for storing data used herein and/or computer programs that are executable by the processor 21. The system memory 22 may include volatile memory such as a random access memory (RAM) 25 and non-volatile memory such as a read only memory (ROM) 24, flash memory, etc., or any combination thereof. The basic input/output system (BIOS) 26 may store the basic procedures for transfer of information between elements of the computer system 20, such as those at the time of loading the operating system with the use of the ROM 24.

The computer system 20 may include one or more storage devices such as one or more removable storage devices 27, one or more non-removable storage devices 28, or a combination thereof. The one or more removable storage devices 27 and non-removable storage devices 28 are connected to the system bus 23 via a storage interface 32. In an aspect, the storage devices and the corresponding computer-readable storage media are power-independent modules for the storage of computer instructions, data structures, program modules, and other data of the computer system 20. The system memory 22, removable storage devices 27, and non-removable storage devices 28 may use a variety of computer-readable storage media. Examples of computer-readable storage media include machine memory such as cache, SRAM, DRAM, zero capacitor RAM, twin transistor RAM, eDRAM, EDO RAM, DDR RAM, EEPROM, NRAM, RRAM, SONOS, PRAM; flash memory or other memory technology such as in solid state drives (SSDs) or flash drives; magnetic cassettes, magnetic tape, and magnetic disk storage such as in hard disk drives or floppy disks; optical storage such as in compact disks (CD-ROM) or digital versatile disks (DVDs); and any other medium which may be used to store the desired data and which can be accessed by the computer system 20.

The system memory 22, removable storage devices 27, and non-removable storage devices 28 of the computer system 20 may be used to store an operating system 35, additional program applications 37, other program modules 38, and program data 39. The computer system 20 may include a peripheral interface 46 for communicating data from input devices 40, such as a keyboard, mouse, stylus, game controller, voice input device, touch input device, or other peripheral devices, such as a printer or scanner via one or more I/O ports, such as a serial port, a parallel port, a universal serial bus (USB), or other peripheral interface. A display device 47 such as one or more monitors, projectors, or integrated display, may also be connected to the system bus 23 across an output interface 48, such as a video adapter. In addition to the display devices 47, the computer system 20 may be equipped with other peripheral output devices (not shown), such as loudspeakers and other audiovisual devices The computer system 20 may operate in a network environment, using a network connection to one or more remote computers 49. The remote computer (or computers) 49 may be local computer workstations or servers comprising most or all of the aforementioned elements in describing the nature of a computer system 20. Other devices may also be present in the computer network, such as, but not limited to, routers, network stations, peer devices or other network nodes. The computer system 20 may include one or more network interfaces 51 or network adapters for communicating with the remote computers 49 via one or more networks such as a local-area computer network (LAN) 50, a wide-area computer network (WAN), an intranet, and the Internet. Examples of the network interface 51 may include an Ethernet interface, a Frame Relay interface, SONET interface, and wireless interfaces.

Aspects of the present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store program code in the form of instructions or data structures that can be accessed by a processor of a computing device, such as the computing system 20. The computer readable storage medium may be an electronic storage device, a magnetic storage device, an optical storage device, an electromagnetic storage device, a semiconductor storage device, or any suitable combination thereof. By way of example, such computer-readable storage medium can comprise a random access memory (RAM), a read-only memory (ROM), EEPROM, a portable compact disc read-only memory (CD-ROM), a digital versatile disk (DVD), flash memory, a hard disk, a portable computer diskette, a memory stick, a floppy disk, or even a mechanically encoded device such as punch-cards or raised structures in a groove having instructions recorded thereon. As used herein, a computer readable storage medium is not to be construed as being transitory signals per se, such as radio waves or other freely propagating electromagnetic waves, electromagnetic waves propagating through a waveguide or transmission media, or electrical signals transmitted through a wire.

Computer readable program instructions described herein can be downloaded to respective computing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network interface in each computing device receives computer readable program instructions from the network and forwards the computer readable program instructions for storage in a computer readable storage medium within the respective computing device.

Computer readable program instructions for carrying out operations of the present disclosure may be assembly instructions, instruction-set-architecture (ISA) instructions, machine instructions, machine dependent instructions, microcode, firmware instructions, state-setting data, or either source code or object code written in any combination of one or more programming languages, including an object oriented programming language, and conventional procedural programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or WAN, or the connection may be made to an external computer (for example, through the Internet). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

In various aspects, the systems and methods described in the present disclosure can be addressed in terms of modules. The term "module" as used herein refers to a real-world device, component, or arrangement of components implemented using hardware, such as by an application specific integrated circuit (ASIC) or FPGA, for example, or as a combination of hardware and software, such as by a microprocessor system and a set of instructions to implement the module's functionality, which (while being executed) transform the microprocessor system into a special-purpose device. A module may also be implemented as a combination of the two, with certain functions facilitated by hardware alone, and other functions facilitated by a combination of hardware and software. In certain implementations, at least a portion, and in some cases, all, of a module may be executed on the processor of a computer system (such as the one described in greater detail in FIG. 5, above). Accordingly, each module may be realized in a variety of suitable configurations, and should not be limited to any particular implementation exemplified herein.

Figure 6:
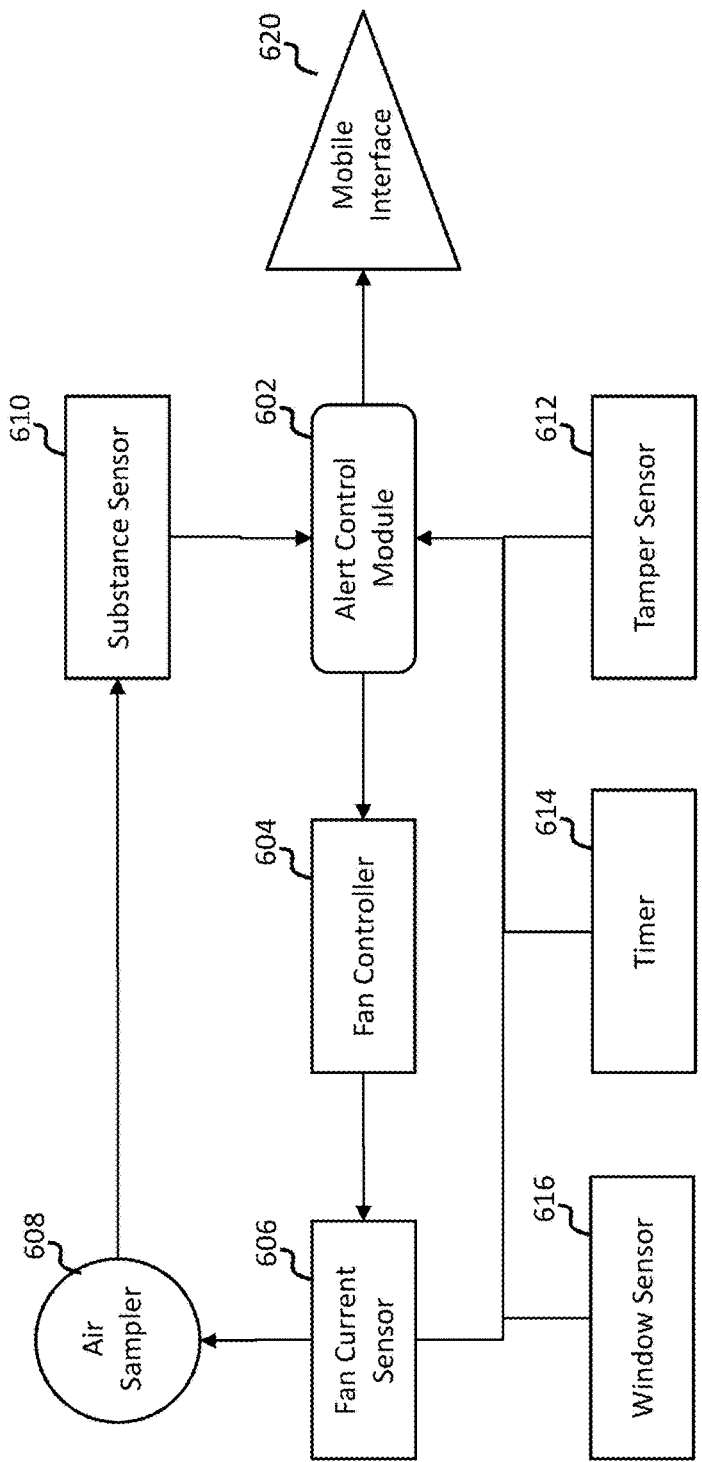
FIG. 6 is a block diagram illustrating a system for detecting inhibited driving, according to exemplary aspects of the present invention.

FIG. 6 is a block diagram illustrating a system 600 for detecting inhibited driving, according to exemplary aspects of the present invention.

According to one aspect, the system 600 comprises an alert control module 602 coupled to a plurality of sensors and controllers: a fan controller 604, a fan current sensor 606, an air sampler 608, a substance sensor 610, a tamper sensor 612, a timer 614 and a window sensor 616. The Alert control module 602 is further coupled to a mobile interface 620 that allows various mobile devices to synchronize with the alert control module 602.

In exemplary aspects, the alert control module 602 is installed in a vehicle that is to be monitored. In some instances, the vehicle may be part of a fleet of vehicles monitored by a fleet manager, while in other instances the vehicle may be monitored by a parent, guardian or the like. The alert control module 602 is notified through various sensors as to the presence of an inhibited driving environment. For example, the substance sensor 610 determines if an inhibiting or intoxicating substance is detected in the cabin of the vehicle. In some aspects, the substance sensor 610 may be an alcohol sensor that detects the presence of alcohol particles in the cabin air of the vehicle. In exemplary embodiments, the alcohol sensor is a passive sensor, though other types of alcohol sensors are contemplated. In one exemplary aspect, the alcohol sensor may be an MQ-3 sensor, though other implementations are also contemplated. However, in other embodiments, the substance sensor 610 may be an opioid detector, a THC detector or the like. In some instances, the various sensors may be included together in system 600 individually, or may be combined on a single chip.

The alert control module 602 may send alerts to one or more coupled mobile devices when an inhibiting substance is detected. In some examples, alerts may be sent to an administrator of a fleet of vehicles such a fleet of trucks, or to parents assigned as administrators over their vehicles. The alert control module 602 may, in some aspects, contain BLUETOOTH or other wireless circuitry along with a vehicle speed sensing module. The mobile interface 620 may transmit alerts to a remote mobile device over a network using a wireless connection such as a Wi-Fi or BLUETOOTH connection. The alert may comprise a text message, an email, a push notification, social media notification, an automated phone call or other type of notification to the remote mobile device that the system 600 has been tampered with or that inhibiting substances have been detected. The present disclosure does not limit the type of notification configurable at the alert control module 602.

In an exemplary aspect, the alert control module 602 signals the fan controller 604 to run at a predetermined default speed to force air into the air sampler 608. In order to determine whether there is activity that is occurring that may inhibit driving, for example a driver or passenger drinking alcohol, inhaling intoxicating substances or the like, the system 600 samples the air in the cabin of the vehicle periodically using air sampler 608, according to a predetermined sample rate configured in the timer 614. In some instances, the default sample rate may be five minutes, though the rate of the timer 614 is configurable by an administrator via the alert control module 602. The air sampler 608 funnels vehicle cabin air into the substance sensor 610 at the predetermined default sample rate.

The alert control module 602 may trigger an air sample and receive and decode the output of the substance sensor 610 to determine if an inhibiting substance is present in the sample. If an inhibiting substance is detected, the air sampling times are shortened to gain more information as to whether the amount is changing over time. An algorithm then determines if an alert is needed. For example, an alert may be sent when the change over time of the substance exceeds a predetermined threshold for a predetermined number of samples. In another example, an alert may be sent when a predetermined level of the substance is continuously detected for a predetermined number of samples.

In one aspect, if the substance sensor 610 detects an inhibiting substance, the alert control module 602 signals the timer 614 to increase the sample rate of the air sampler 608. For example, the rate may be increased to take a sample every two minutes. If after this rate increase, the substance sensor 610 detects an inhibiting substance in the cabin air using the substance sensor 610 a predetermined number of times (e.g., five times, configurable via the alert control module 602), the alert control module 602 is signaled to alert an administrator via the mobile interface 620.

According to one aspect, the air sampler 608 comprises a small DC motor and fan that, when activated, draw air through a plenum directly into the substance sensor 610 for sampling. In some aspects, the air sampler 608 can be triggered by any one of the alert control module 602, the tamper sensor 612, the timer 614, or the window sensor 616.

A driver may attempt to decrease the inhibiting substance in the air or thwart the system 600 entirely by disconnecting its components or placing the system 600 or components therein in a different location, such as a glove compartment, trunk or the like to avoid inhibiting substance detection. The system 600 provides various sensors to detect such positional displacements or attempts to change the configuration of the system.

According to exemplary aspects of the disclosure, the system 600 comprises a fan current sensor 606, a tamper sensor 612, and a window sensor 616. The fan controller 604 may be coupled to the fan current sensor 606 that determines whether the fan has been tampered with, based on current or power loss. The fan current sensor 606 measures the current flowing through the fan to determine whether the power has been cut. If such a loss in power or current is detected, the fan controller 604 signals the alert control module 602 to generate an alert to send out to the administrator.

The tamper sensor 612 may detect any tampering in the system such as movement, change of circuitry or the like. The tamper sensor 612 may comprise a geolocation sensor, a movement sensor, an accelerometer, or any sensor that can determine that the system 600 has been moved or the air has changed in some way. Examples of tampering might be taping over the air intake port or somehow jamming the fan blades that draw air into the system 600. Tampering may trigger an alert in the alert control module 602 or may trigger the air sampler 608 to take air samples. The alert control module 602 then issues an alert to administrator selected to receive such alerts using mobile interface 620.

A driver may attempt to subvert the system 600 by, for example, decreasing the inhibiting substance detected in the air samples by opening a window. The window sensor 616 determines whether the window has been opened to allow fresh air into the vehicle. In some aspects, the window sensor 616 may be implemented as a wind sensor, pressure sensor, pressure differential sensor or the like. The window sensor 616 may automatically trigger an air sample by the air sampler 608 when a change in barometric (air) pressure inside the vehicle is detected or an increase in wind noise level is detected. In other instances, an air sample may be triggered when the window sensor 616 detects that the window has been opened for a predetermined period of time. This may comprise determining an increase in sound volume associated with the frequency of wind noise in a moving vehicle.

In the various ways described above, inhibiting substances such as alcohol, THC or the like, may be detected using the system 600 and an administrator alerted to their presence in a vehicle cabin. Further, attempts to subvert or tamper with the system 600, or tamper with the air sample collections will be monitored and alerted, or may trigger a sample collection. Accordingly, an effective means to monitor driver behavior in a vehicle is contemplated.

According to some exemplary aspects, the mobile interface 620 may be a mobile phone itself that connect to the alert control module 602 directly, or via BLUETOOTH or other means of wired/wireless technology. The mobile device receives a signal from the alert control module 602 and configures an alert in the form of a message, a phone call, an email, a push notification or the like, to an administrator of the system to alert them to the possibility of inhibited driving.

Figure 7:
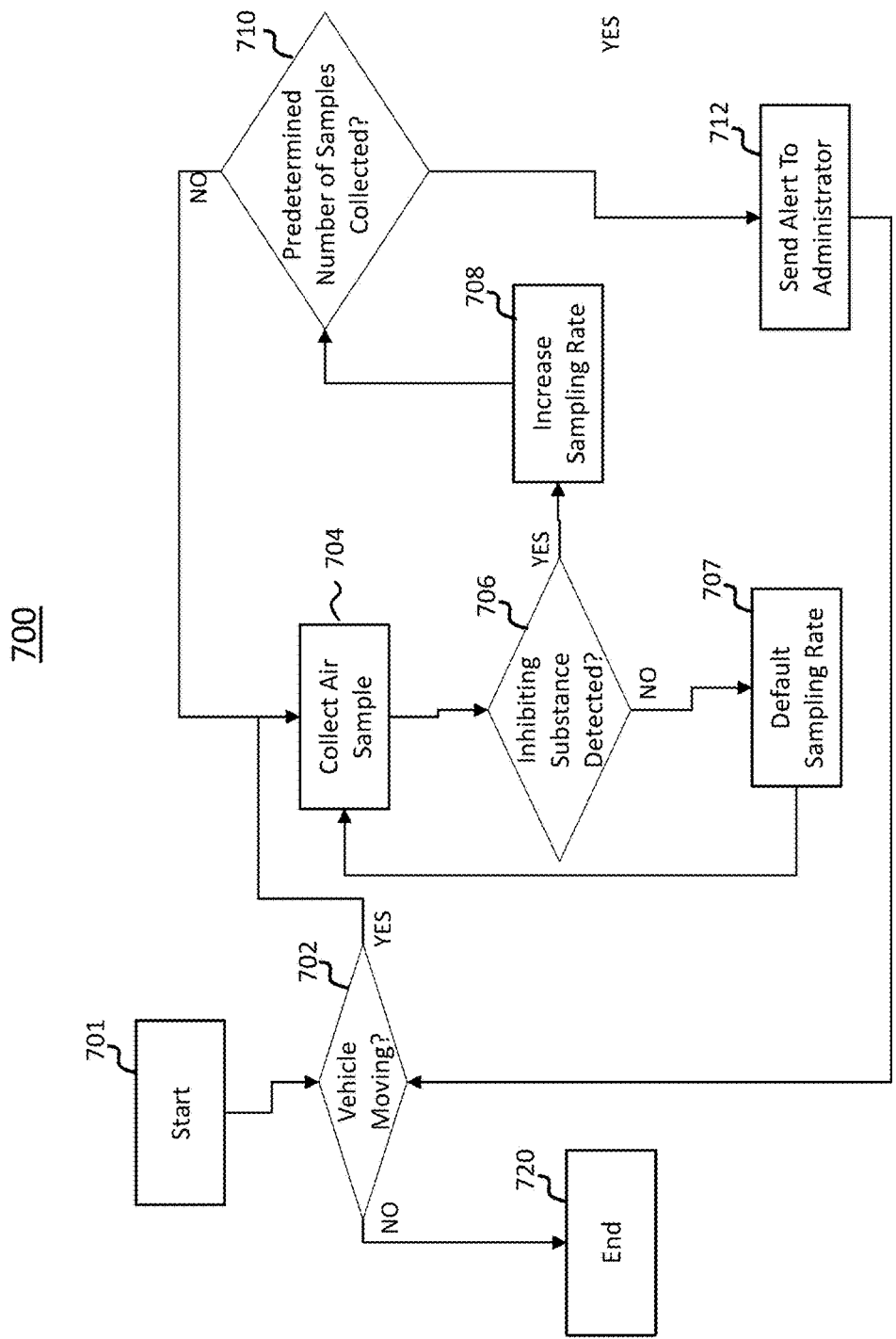
FIG. 7 is a flow diagram for a method for detecting inhibited driving, according to exemplary aspects of the present invention.

FIG. 7 is a flow diagram for a method 700 for detecting inhibited driving, according to exemplary aspects of the present invention. The method 700 begins at 701 when the operation is initiated as described above and proceeds to 702 as shown.

At 702, the alert control module 603 determines whether the vehicle is moving. If the vehicle is not moving, the method ends at 720. Otherwise, the method 700 proceeds to 704.

Then at 704, an air sampler, e.g., air sampler 608 of FIG. 6, collects air samples according to a predetermined sampling rate. In some aspects, the default sampling rate is four minutes, though other rates are also contemplated. Accordingly, every four minutes, the air sampler will collect an air sample.

At 706, a substance sensor, e.g. substance sensor 610, determines whether an inhibiting substance has been detected in the air sample. In some aspects, the intoxicant may be alcohol, methamphetamines, or any other intoxicant or substance that inhibits the drivers' ability in any way, including driving, vision, hearing or the like.

If the initial sample at 704 is determined to be an inhibiting substance at 706, the method proceeds to 708 where the sampling rate of the air sampler is increased in order to avoid false positives. In this instance, if an initial air sample detected an inhibiting substance, then the system 600 must determine whether this was an error, or a positive sample. In some aspects, the air sampler may be controlled to sample every one or two minutes instead of every 4 minutes, according to a predetermined configuration.

If at 706, an inhibiting substance is not detected, the method proceeds to 707, where the sampling is set to collect at the default sampling rate. Subsequently the method proceeds to 704 to collect further samples.

At 710, the method 700 determines whether a predetermined number of samples have been detected to contain inhibiting substance. In some aspects, the predetermined number is five, though other threshold samples are contemplated. According to this aspect, the predetermined threshold is selected as a controlling measure to verify that samples are correctly determined to contain inhibiting substances or the samples were merely false positives.

If at 710, the predetermined threshold has not been collected yet, the method proceeds to 704. Otherwise, if the method 700 has determined that a predetermined threshold contain an inhibiting substance, the method proceeds to 712 where the method 700 sends an alert to an administrator. The method then returns to 702 to determine if the vehicle is moving.

Figure 8:
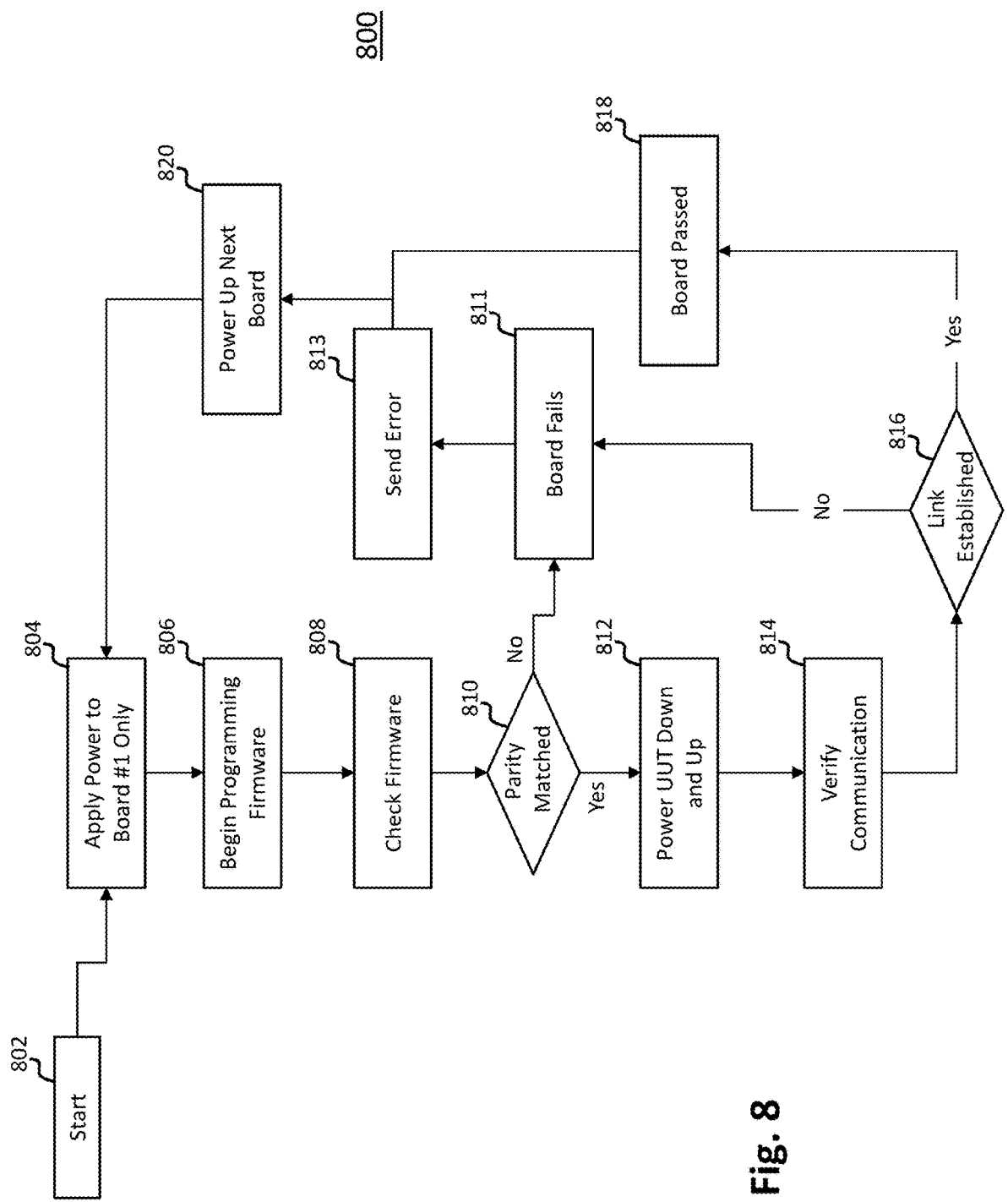
FIG. 8 is a flow diagram for a method for testing the system of FIG. 6, according to exemplary aspects of the present invention

FIG. 8 illustrates a flow diagram for a method for testing the system 600 according to an exemplary aspect of the present disclosure.

In exemplary aspects, an automated In Circuit Test (ICT) system (e.g., Teradyne Z1880) is used to test and load software onto the System 600 to insure the system functions prior to final assembly.

The method begins at 802 and proceeds to 804 where power is applied to a first circuit board (e.g., a component of system 600). During manufacture of the assemblies for system 600, panels of up to ten boards per panel are used, and each board is powered up one at a time.

At 806, the programming of the firmware begins. In some aspects, the programming is supplied as a HEX file, though the present disclosure is not limited thereto.

At 808, the method 600 checks whether the firmware is loaded correctly to the first circuit board using, for example, a parity check.

If the firmware is not loaded correctly at 810, the method proceeds to 811 where the board is considered to have failed. An error message is sent to the engine computer at 813, and the method proceeds to power up the next board at 820. In other words, when the current board is finished being tested, the ICT powers up the next board in the panel mentioned with respect to 804 until the entire panel has been tested.

However, if at 810, the parity matched, the method proceeds to 812, where the Unit Under Test (UUT) is powered down and then powered back up again. The method proceeds to 812 to verify that the UUT communicates with the test fixture (e.g., a mobile device) via predetermined communication methods such as BLUETOOTH or the like.

At 814, the method determines whether a link has been established with the test fixture. If not, the method returns to 811 whether the board is considered to have failed. Otherwise, the method proceeds to 816 where the board is considered to have passed. Subsequently, the next board is powered up at step 818.

In various aspects, the systems and methods described herein may be implemented in hardware, software, firmware, or any combination thereof. If implemented in software, the methods may be stored as one or more instructions or code on a non-transitory computer-readable medium. Computer-readable medium includes data storage. By way of example, and not limitation, such computer-readable medium can comprise RAM, ROM, EEPROM, CD-ROM, Flash memory or other types of electric, magnetic, or optical storage medium, or any other medium that can be used to carry or store desired program code in the form of instructions or data structures and that can be accessed by a processor of a general purpose computer.

In the interest of clarity, not all of the routine features of the aspects are disclosed herein. It will be appreciated that in the development of any actual implementation of the present disclosure, numerous implementation-specific decisions must be made in order to achieve the developer's specific goals, and that these specific goals will vary for different implementations and different developers. It will be appreciated that such a development effort might be complex and time-consuming, but would nevertheless be a routine undertaking of engineering for those of ordinary skill in the art having the benefit of this disclosure.

Furthermore, it is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of the skilled in the relevant art(s). Moreover, it is not intended for any term in the specification or claims to be ascribed an uncommon or special meaning unless explicitly set forth as such.

The various aspects disclosed herein encompass present and future known equivalents to the known modules referred to herein by way of illustration. Moreover, while aspects and applications have been shown and described, it would be apparent to those skilled in the art having the benefit of this disclosure that many more modifications than mentioned above are possible without departing from the inventive concepts disclosed herein.

What is claimed is:

1. A method for monitoring a vehicle for inhibiting substances comprising:
   detecting, using a movement detector, movement of a vehicle;
   collecting, using an air sampler, an initial air sample of air within a cabin of the vehicle;
   analyzing, using an inhibiting substance detector, the air sample to determine whether an inhibiting substance is detected in the air sample;
   in response to determining that an inhibiting substance is detected in the air sample, increasing the sampling rate of the air sampler, until a predetermined number of samples are collected that also have been analyzed and an inhibiting substance detected therein;
   sending an alert to an administrator of the vehicle indicating that inhibited driving is occurring;
   detecting, using a window sensor, that a window has been opened in the vehicle; and
   triggering an air sample collection by the air sampler to determining the presence of an inhibiting substance upon determining that the window in the vehicle is open.

2. The method of claim 1, wherein detecting the window has been opened comprises:
   detecting air pressure or an increase in wind noise level within the cabin of the vehicle;
   determining that the air pressure is different from air pressure outside of the vehicle; or
   determining an increase in sound volume associated with the frequency of wind noise in a moving vehicle.

3. The method of claim 2, further comprising:
   sending an alert to the administrator of the vehicle indicating that a subversion attempt has occurred.

4. The method of claim 1, further comprising:
   detecting tampering, using a tamper sensor, of the air sampler and the window sensor;
   triggering an air sample collection by the air sampler to determining the presence of an inhibiting substance.

5. The method of claim 4, further comprising:
   sending an alert to the administrator of the vehicle indicating that a subversion attempt has occurred.

6. The method of claim 4, wherein tamper sensor detects movement of the air sampler, or current to a fan of the air sampler to determine whether tampering has occurred.

7. The method of claim 1, further comprising:
   in response to analyzing one of the predetermined number of samples and determining the one sample does not contain an inhibiting substance, returning the sampling rate to a default sampling rate.

8. The method of claim 7, wherein the default sampling rate is approximately five minutes, and the increased sampling rate is approximately two minutes.

9. The method of claim 1, wherein the predetermined number of samples is five.

10. A system for monitoring a vehicle for inhibiting substances comprising:
    a movement detector configured to detect movement of a vehicle;
    a window sensor configured to detect when a window has been opened in the vehicle;
    an air sampler, coupled to the movement detector, configured to collect an initial air sample of air within a cabin of the vehicle;
    an inhibiting substance detector configured to analyze the air sample to determine whether an inhibiting substance is detected in the air sample; and
    a processor configured to:
       in response to determining that an inhibiting substance is detected in the air sample, increase the sampling rate of the air sampler, until a predetermined number of samples are collected that also have been analyzed and an inhibiting substance detected therein;
       send an alert to an administrator of the vehicle indicating that inhibited driving is occurring; and
       trigger the air sampler to perform an air sample collection to determine the presence of the inhibiting substance when the window sensor detects the window has been opened.

11. The system of claim 10, wherein detecting the window has been opened comprises:
    detecting air pressure or an increase in wind noise level within the cabin of the vehicle;
    determining that the air pressure is different from air pressure outside of the vehicle; or determining an increase in sound volume associated with the frequency of wind noise in a moving vehicle.

12. The system of claim 11, wherein the processor is further configured to:
send an alert to the administrator of the vehicle indicating that a subversion attempt has occurred.

13. The system of claim 10, further comprising:
a tamper sensor configured to detect tampering with the air sampler and the window sensor,
wherein the air sampler is then triggered to perform air sample collection to determine the presence of an inhibiting substance.

14. The system of claim 13, wherein the processor is further configured to:
send an alert to the administrator of the vehicle indicating that a subversion attempt has occurred.

15. The system of claim 13, wherein tamper sensor detects movement of the air sampler, or current to a fan of the air sampler to determine whether tampering has occurred.

16. The system of claim 10, wherein the processor is further configured to:
in response to analyzing one of the predetermined number of samples and determining the one sample does not contain an inhibiting substance, return the sampling rate to a default sampling rate.

17. The system of claim 16, wherein the default sampling rate is approximately five minutes, and the increased sampling rate is approximately two minutes.

18. The system of claim 10, wherein the predetermined number of samples is five.

19. A system for monitoring a vehicle for inhibiting substances comprising:
a window sensor configured to detect when a window has been opened in the vehicle based on a change in barometric pressure inside the vehicle;
an air sampler configured to collect an initial air sample of air within a cabin of the vehicle;
an inhibiting substance detector configured to analyze the air sample to determine whether an inhibiting substance is detected in the initial air sample; and
a processor configured to:
trigger the air sampler to collect the initial sample when the window sensor detects the window has been opened,
in response to determining that an inhibiting substance is detected in the initial air sample, increase the sampling rate of the air sampler, until a predetermined number of samples are collected that are also analyzed to confirm the inhibiting substance is detected therein; and
send an alert to an administrator of the vehicle indicating that inhibited driving is occurring based on the detected inhibiting substance.

* * * * *